United States Patent [19]

Muller et al.

[11] Patent Number: 5,437,658
[45] Date of Patent: Aug. 1, 1995

[54] METHOD AND SYSTEM FOR LASER THERMOKERATOPLASTY OF THE CORNEA

[75] Inventors: David F. Muller, Boston; Alex C. Sacharoff, Framingham, both of Mass.

[73] Assignee: Summit Technology, Incorporated, Waltham, Mass.

[21] Appl. No.: 957,702

[22] Filed: Oct. 7, 1992

[51] Int. Cl.⁶ .............................................. A61N 5/06
[52] U.S. Cl. ........................................ 606/5; 606/17; 606/4
[58] Field of Search ................. 606/4, 5, 6, 16, 17; 128/898

[56] References Cited

U.S. PATENT DOCUMENTS

| | | | |
|---|---|---|---|
| 4,583,539 | 4/1986 | Karlin et al. | |
| 4,732,148 | 3/1988 | L'Esperance, Jr. | 606/5 |
| 4,860,743 | 8/1989 | Abela | |
| 4,880,001 | 11/1989 | Weinberg | 606/11 |
| 4,917,084 | 4/1990 | Sinofsky | 606/7 |
| 4,976,709 | 12/1990 | Sand | 606/5 |
| 5,009,660 | 4/1991 | Clapham | 606/166 |

(List continued on next page.)

FOREIGN PATENT DOCUMENTS

| | | | |
|---|---|---|---|
| 484005 | 5/1992 | European Pat. Off. | |
| 2819781 | 9/1979 | U.S.S.R. | A61F 9/00 |
| WO89/06519 | 7/1989 | WIPO | |

OTHER PUBLICATIONS

J. James Rowsey et al., "Los Alamos Keratoplasty Technique", *Contact Lens*, vol. 6, No. 1, pp. 1–12, Jan./Mar. 1980.

Albert C. Neumann et al., "Hyperopic thermokeratoplasty: Clinical evaluation", *J Cataract Refract Surg.* vol. 17, pp. 830–838, Nov. 1991.

J. M. Parel et al. "Laser Photo Thermal Keratoplasty (LPTK)" *Refractive and Corneal Surgery*, (Abstract) vol. 7, p. 408, 1991.

James V. Aquavella, "Thermokeratoplasty", *Ophthalmic Surgery*, vol. 5, No. 1, pp. 39–47, Spring 1974.

Gerald Horn et al., "New refractive method for laser thermal keratoplasty with the Cl:MgF₂ laser", *J. Cata-*
(List continued on next page.)

Primary Examiner—Stephen C. Pellegrino
Assistant Examiner—Sonya C. Harris
Attorney, Agent, or Firm—Fish & Richardson

[57] ABSTRACT

The invention is a system and method for modifying the corneal curvature by irradiating the cornea to deliver thermal energy to the stroma. The system includes multiple irradiation ports for introducing electromagnetic radiation of a wavelength suitable for absorption in the stroma; positioning means, such as a hemi-spherical dome with several tracks for positioning the irradiation ports, respectively, at locations of a preselected geometric pattern relative to the pretreated cornea, the geometric pattern being selected to correspond to a desired modified shape of the cornea; transmission means adapted to deliver controlled amounts of the radiation from a radiation source to each of the irradiation ports; and the irradiation ports, positioned at the locations of the geometric pattern, constructed to introduce the radiation to treatment volumes of the stroma in a cooperative manner to induce desired shrinkage of the collagenous stromal tissue and cause change in the corneal curvature. Each treatment volume, formed by a radiation pattern emanating from one irradiation port or by intersection of radiation patterns emanating from multiple irradiation ports, is created in a controllable manner to have a desired volume and energy profile. The transmission means that includes fiber optic waveguides are connected to distribution means for dispensing controlled amounts of the radiation to each of the fiber optic waveguides. The system also includes inspection means for observing and evaluating the shrinkage of collagenous tissue.

56 Claims, 12 Drawing Sheets

U.S. PATENT DOCUMENTS

| | | | |
|---|---|---|---|
| 5,019,074 | 3/1991 | Muller | 606/5 |
| 5,133,708 | 7/1992 | Smith | 606/5 |
| 5,152,759 | 10/1992 | Parel et al. | 606/5 |
| 5,263,950 | 11/1993 | L'Esperance, Jr. | 606/6 |
| 5,263,951 | 11/1993 | Spears et al. | 606/12 |

OTHER PUBLICATIONS

*ract Refract Surgery*, vol. 16, pp. 611–616, Sep. 1990.

Ronald A. Schachar, "Radial Thermokeratoplasty", pp. 47–57.

Albert C. Neumann et al., "Effect of thermokeratoplasty on corneal curvature", *J Cataract Refract Surg*, vol. 16, pp. 727–731, Nov. 1990.

Albert C. Neumann et al., "Radial Thermokeratoplasty for the Correction of Hyperopia", *Refractive & Corneal Surgery*, vol. 6, pp. 404–412, Nov./Dec. 1989.

Peter J. McDonnell and Albert C. Neumann et al., "Radial Thermokeratoplasty For Hyperopia", *Refractive & Corneal Surgery*, vol. 5, pp. 50–54, Jan./Feb. 1989.

Sandy T. Feldman et al., "Regression of Effect Following Radial Thermokeratoplasty in Humans", *Refractive and Corneal Surgery*, vol. 5, pp. 288–291, Sep./Oct. 1989.

David Stern et al., "Infrared Laser Surgery of the Cornea", Studies with a Raman-shifted Neodymium: YAG Laser at 2.80 and 2.92 $\mu m$", *Ophthalmology*, pp. 1434–1441, vol. 94, No. 10, Oct. 1988.

Peter Gruenberg et al., "Increase in Rabbit Corneal Curvature by Heated Ring Application", *Annals of Ophthalmology*, pp. 67–70; Jan. 1981.

Joel M. Krauss et al., "Laser Interactions with the Cornea", *Survey of Ophthalmology*, vol. 31, No. 1, pp. 37–53 Jul.–Aug. 1986.

Antonio R. Gasset et al., "Thermokeratoplasty", *TR AM ACAD Ophthalmology & Otolaryngology*, vol. 77, pp. OP441–OP454, Jul.–Aug. 1973.

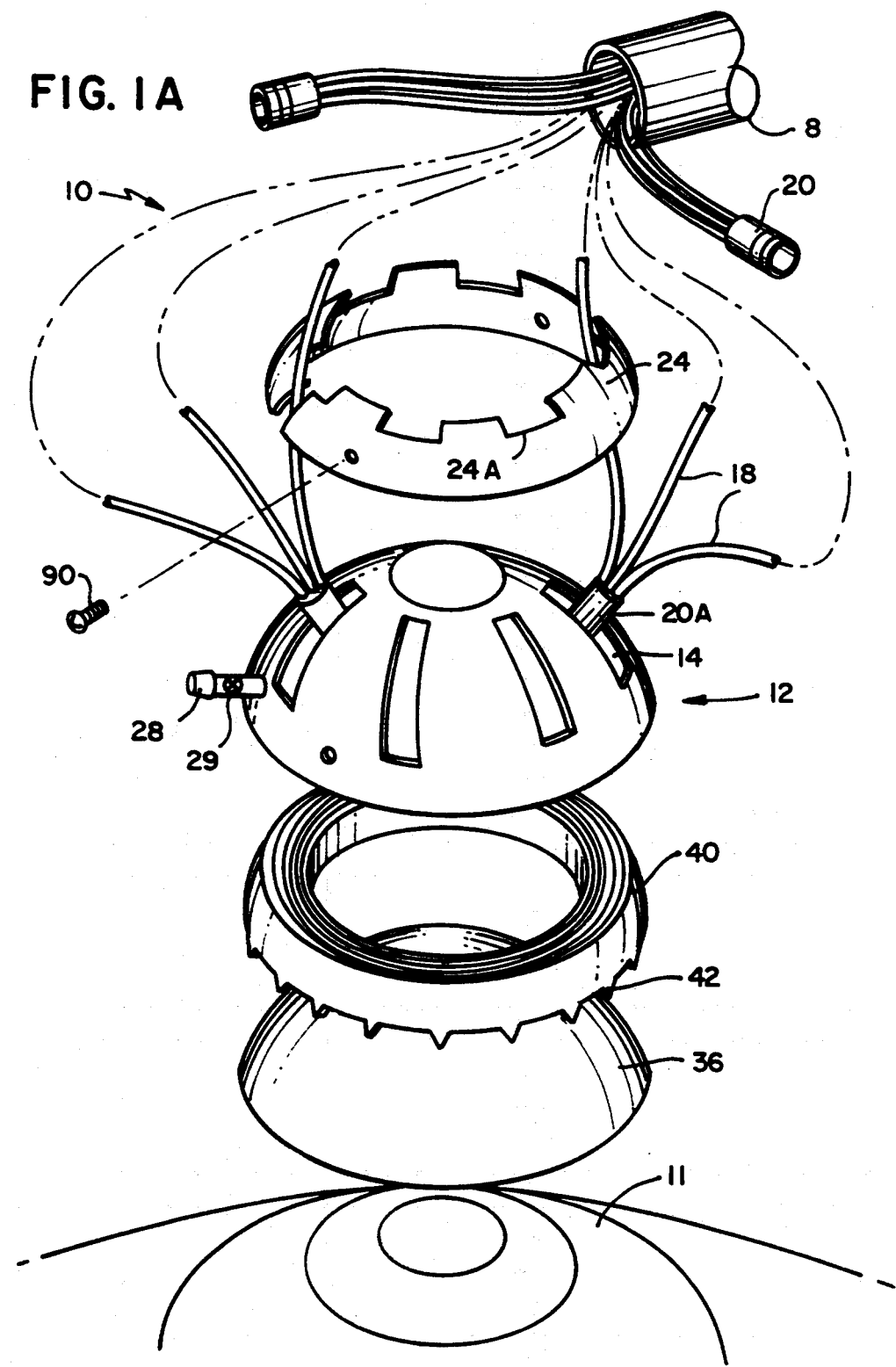

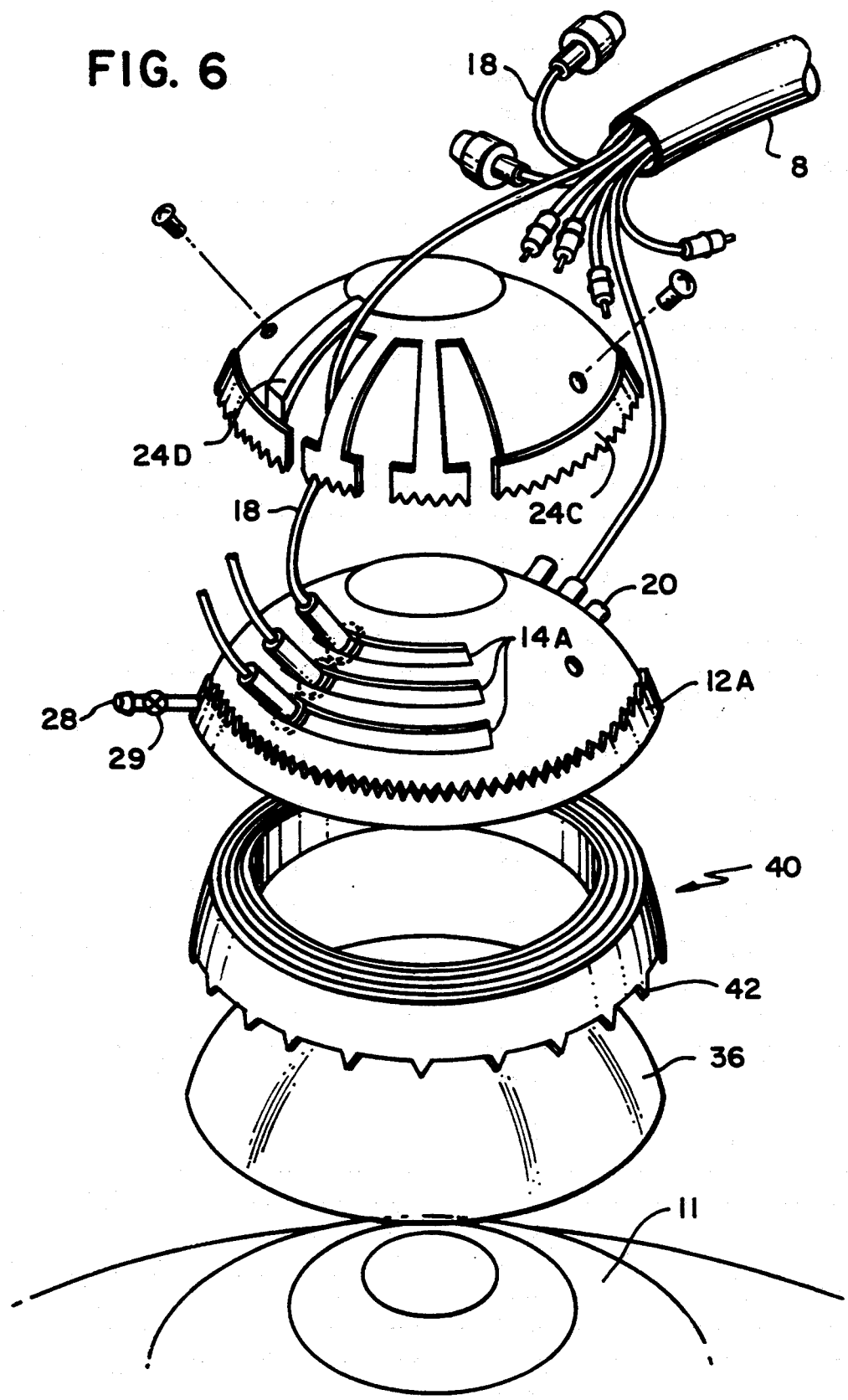

METHOD AND SYSTEM FOR LASER THERMOKERATOPLASTY OF THE CORNEA

BACKGROUND OF THE INVENTION

The invention relates to controllable, reproducible, nonsurgical alteration of the corneal curvature in the human eye.

Refractive errors of the eye such as hyperopia, myopia, and astigmatism are widespread in the human population. The cornea which accounts for most of the refractive power of the eye comprises transparent avascular tissue that forms the anterior portion of the eye. It resides in the sclera at the limbus. The transparency of the cornea is due to its uniform structure, avascularity, and deturgescence, which is the state of relative hydration of the corneal tissue. The average adult cornea is about 0.65 mm thick at the periphery and about 0.50 mm thick in the center. From anterior to posterior, the cornea has the following five distinct layers: the epithelium, Bowman's membrane, the stroma, Descemet's membrane, and the endothelium.

The present invention concerns hydrothermal shrinkage of collagen fibers present in the stroma. The corneal stroma accounts for about 90% of the corneal thickness; it is composed of intertwining lamellar fibers that are about 1 $\mu$m wide and run almost the full diameter of the cornea. The lamellar fibers run parallel to the surface of the cornea and by virtue of their size and periodicity are optically clear. Collagen is a protein found in connective tissues of many organs of the human body including the corneal stroma. The connective tissue of the corneal stroma possesses high transparency of cross-oriented individual sheets, or lamellae of collagen, with a high water content and small content of protein and mucopolysaccharides. The intermolecular cross-links provide the collagen fibers with unique physical properties of high tensile strength and substantial elasticity. The extracellular matrix of the corneal connective tissue consists of complex macromolecules, the biosynthesis of which involves several specific reactions that are often under stringent enzymatic control. The cross-linking of collagen fibers can be inhibited by supplying energy to the matrix. The net generation of collagen connective tissue is then dependent on the precise balance between the synthesis and degradation of the above mentioned enzyme.

The hydrothermal shrinkage property of collagen fibers has been recognized for many years. At increased temperatures, the collagen ultrastructural stabilizing cross-links rupture resulting in immediate contraction of the fibers to about ⅓ of their original linear dimension. At the same time the caliber of individual fibers increases; however, the structural integrity of the connective tissue is maintained. The shrinkage changes the overall shape of the cornea and thus changes the refractive power of the eye; this is utilized in thermokeratoplasty. This corneal recurving procedure requires a predictable collagen shrinkage and thus predictable change in the cornea shape. This should be achieved without damaging either Bowman's membrane or Descemet's membrane. One disadvantage of the above described thermal reshaping of the corneal profile could be rapid replacement of contracted collagen fibers by new mature collagen fibers of original length. This replacement is most pronounced in traumatic injuries of the eye. However, if atraumatic collagen shrinkage is achieved, it is believed that a protracted or permanent recurving of the cornea occurs.

In the past, various thermokeratoplastic techniques have been suggested. Shrinkage of the collagen fibers was achieved by applying RF current, inserting a hot microwire into the stroma, heating appropriate areas of the stroma using laser energy, or placing a surface of a hot instrument onto the eye surface. Many of these methods pose a high risk of damage to the epithelium and Bowman's membrane on the anterior side of the cornea, as well as Descemet's membrane and the endothelium on the posterior side of the cornea. Thus, it is very important to precisely control the amount of heat applied to the stroma. Sufficient heat must be delivered to cause permanent fiber shrinkage. However, if too much heat is applied, then permanent damage to Bowman's and Descemet layers can occur.

Different types of corrective procedures can be performed by selectively heating the stroma and causing selective shrinkage of the stromal collagen. Hyperopic corrections are achieved by causing shrinkage of the collagen in a ring-shaped pattern about the optical axis of the eye. Large hyperopic corrections are usually achieved by applying several concentrically arranged ring patterns. Astigmatism can be treated by applying accurate segments of the full treatment rings used for spherical hyperopia with the arcs centered on the flat meridian of the cornea. Myopic corrections can be achieved by central application of a focused energy beam in order to flatten the corneal shape or by application of radial patterns. In an eye which has several refractive errors a combination of several patterns can be used. Thus, it is necessary to select an appropriate geometric pattern corresponding to the shape of the corneal curvature prior to the laser thermokeratoplasty and deliver heat precisely to the selected locations.

Currently, laser thermokeratoplasty is performed by applying a handpiece to the corneal surface in order to irradiate the cornea. To denote the appropriate locations, a ring marker has been used to mark the cornea with a dye. Then, the ophthalmologist positions the handpiece on the marked site and irradiates the cornea. A series of focused exposures are made sequentially on the marked sites. The introduced radiation is focused to a depth of less than 450 $\mu$m and is absorbed in the stroma. The plurality of focused conical exposures creates reformation of the cornea. Even though marking of the exposure sites using the dye gives some precision and reproducibility to this corrective procedure, the result of the laser thermokeratoplasty depends to a great extent on the skill of the ophthalmologist performing the procedure. Furthermore, since desired results of the laser thermokeratoplasty depend on appropriate energy delivery to the number of predetermined sites on the eye surface, and on the skills of the ophthalmologist, laser thermokeratoplasty, as currently performed, requires a high degree of tactile skill.

In summary, there continues to be a need for a surgical device and procedure which can deliver thermal energy to precisely defined locations in the stroma, for an exactly controlled amount of time, performed in a standardized manner, very quickly and without causing damage to the cornea.

SUMMARY OF THE INVENTION

In general, the invention features a fiberoptic system for performing laser thermokeratoplasty. The system delivers thermal energy by irradiating precisely defined locations in the stroma to cause coagulation and shrinkage of the collagen connective tissue of the stroma. The system precisely controls the locations and the amount of energy delivered to the stroma in order to prevent damage to the epithelium and Bowman's membrane on the anterior side of the cornea, as well as Descemet's membrane and the endothelium on the posterior side of the cornea. The system enables reproducible performance of laser thermokeratoplasty.

According to one important aspect, the invention is a system method for modifying the corneal curvature by irradiating the cornea to deliver thermal energy to the stroma, the system comprising multiple irradiation ports adapted to introduce to the stroma electromagnetic radiation of a wavelength suitable for absorption in the stroma; positioning means adapted to position the irradiation ports respectively at preselected relationships to the pretreated cornea, the relationships being selected to correspond to a desired modification of the cornea; transmission means adapted to deliver controlled amounts of the radiation from a radiation source to each of the irradiation ports; and the irradiation ports, positioned at the preselected relationships, constructed to introduce the radiation to controlled volumes of the stroma in a cooperative manner to induce desired shrinkage of the collagenous stromal tissue to cause change in the corneal curvature.

Preferred embodiments of this aspect of the invention may have one or more of the following features.

The positioning means are adapted to position the irradiation ports on a preselected geometric pattern relative to the pretreated shape of the cornea to create a specific distribution of treatment volumes in each of which the desired shrinkage can occur.

Each of the treatment volumes is formed by a radiation pattern emanating from one irradiation port.

The desired shrinkage occurs in a volume formed by intersection of radiation patterns emanating from at least two irradiation ports, energy carried by a single radiation pattern being substantially below the energy necessary for shrinkage of the collagenous stromal tissue, the intersecting radiation patterns forming a treatment volume having sufficient energy to induce shrinkage of the collagenous stromal tissue.

Each of the treatment volumes is formed by intersection of radiation patterns emanating from at least two irradiation ports, energy carried by a single radiation pattern being substantially below the energy necessary for shrinkage of the collagenous stromal tissue, the intersecting radiation patterns supplying sufficient energy to the treatment volume to induce shrinkage of the collagenous stromal tissue.

Energy profile within the treatment volume may be varied in a controllable manner by attuning the intersection of the treatment volumes.

The positioning means are further adapted to move the irradiation ports to selected different locations on the geometric pattern.

The positioning means are further adapted to move the irradiation ports continually along a path while simultaneously introducing the radiation to the stroma in order to form the treatment volumes, the path being chosen in correlation with the preselected geometric pattern.

Preferred embodiments of this aspect of the invention may also include one or more of the following.

Positioning means that are constructed to be attached to the corneal surface in a desired relationship to the pretreated corneal shape to position the irradiation ports accurately with respect to the distribution of treatment volumes of the stroma.

Prophylactic means placed between the corneal surface and the positioning means.

The prophylactic means comprise optical interface matching means adapted to couple the radiation from the irradiation ports to the cornea without substantial loss.

The positioning means includes eye fixation means adapted to hold the positioning means at a selected location on the corneal surface while preventing movement of the globe of the eye.

The eye fixation means comprise a thornton ring attached to the corneal surface by relatively small protrusions.

In preferred embodiments of this aspect of the invention, each irradiation port may include focusing means adapted to modify the radiation pattern to focus the absorbable radiation within the stroma of the eye.

The focusing means are further adapted to create in a controllable manner the treatment volumes with variable energy profile.

The focusing means are further adapted to focus the radiation to a desired depth.

The focusing means may comprise a lens system, a convergent fiber optic wave guide or a self-focusing fiber optic wave guide.

Preferred embodiments of this aspect of the invention may have one or more of the following features.

The transmission means comprise a set of fiber optic wave guides connected respectively to the multiple irradiation ports and adapted to transmit the radiation from a radiation source to the multiple irradiation ports.

Each irradiation port is positioned at a selected location on a preselected geometric pattern relative to the pretreated shape of the cornea and adapted to introduce a radiation pattern that forms the treatment volume.

The transmission means include distribution means adapted to distribute desired amounts of energy in a predetermined sequence to each of the irradiation ports from the radiation source.

A set of the irradiation ports that are geometrically ordered to each other and each connected to the fiber optic waveguide, are positioned at the same time at a selected location on the preselected geometric pattern relative to the pretreated shape of the cornea, the set of geometrically ordered irradiation ports being adapted to introduce radiation patterns that form the treatment volume at their intersection, each of the introduced radiation patterns having energy substantially below the energy necessary for shrinkage of the collagenous stromal tissue, the treatment volume having energy sufficient to induce shrinkage of the collagenous stromal tissue.

The transmission means include distribution means adapted to distribute simultaneously desired amounts of energy to one said set of irradiation ports at a time.

The transmission means comprise distribution means adapted to distribute desired amounts of energy simultaneously to all fiber optic waveguides from the radiation source.

Preferred embodiments of this aspect of the invention may have one or more of the following features.

The irradiation ports comprise optical interface matching means adapted to couple the radiation to the cornea without substantial radiation loss. The optical interface matching means includes a fluid medium.

Preferred embodiments of this aspect of the invention may include positioning means that comprise a rigid hemi-spherically shaped member adapted to be placed upon the corneal surface in a desired relationship to the pretreated corneal shape; at least two tracks located in the rigid member at spaced apart positions, each adapted to retain at least one the irradiation port within the rigid member and adapted to enable movement of the irradiation port to selected different locations; and a holding member adapted to hold the irradiation ports at the locations within the tracks, the holding member enabling the ports to reside in the geometric pattern.

The positioning means may further comprise a ring shaped member having small protrusions constructed to be affixed to the corneal surface, the ring shaped member being connectable to the rigid hemi-spherically shaped member and being adapted to maintain the irradiation ports at the locations while preventing movement of the globe of the eye.

The positioning means may further comprise a membrane located between the corneal surface and the ring shaped member adapted to transmit light to the cornea from the irradiation ports.

According to another important aspect, the invention is a system for modifying the corneal curvature by irradiating the cornea to deliver thermal energy to the stroma, the system comprising multiple irradiation ports adapted to introduce to the stroma electromagnetic radiation of a wavelength suitable for absorption in the stroma; a rigid hemi-spherically shaped member adapted to be placed upon the corneal surface in a desired relationship to the pretreated corneal shape; at least two tracks located in the rigid member at spaced apart positions, each adapted to retain at least one the irradiation port within the rigid member and adapted to enable movement of the irradiation port to selected different locations on a geometric pattern, the geometric pattern being selected to correspond to a desired modified shape of the cornea; a holding member adapted to hold the irradiation ports at the locations within the tracks, the holding member enabling the ports to reside in the geometric pattern; a ring shaped member having small protrusions constructed to be affixed to the corneal surface, the ring shaped member being connectable to the rigid spherically shaped member to maintain the irradiation ports at the locations; a set of fiber optic wave guides connected respectively to the multiple irradiation ports and adapted to transmit the radiation from a radiation source to the multiple irradiation ports; distribution means adapted to distribute controlled amounts of the radiation from a radiation source to each of the respective fiber optic wave guides connected to the irradiation ports; and the irradiation ports, positioned at the selected locations, constructed to introduce the radiation to be absorbed in selected treatment volumes of the stroma to induce shrinkage of the collagenous stromal tissue and cause change in the corneal curvature to the desired modified shape.

Preferred embodiments of this aspect of the invention may have one or more of the following features.

The ring shaped member is adapted to be connected by substantial vacuum to the rigid hemi-spherically shaped member.

The ring shaped member is connectable to the rigid hemi-spherically shaped member in a manner that enables relative rotational movement of the two members.

The system further includes computer control means adapted to govern distribution of the radiation from the source to each irradiation port in accordance with locations of the irradiation ports and the desired modification of the cornea.

The treatment volumes have substantially conical shape.

The treatment volumes of the stroma are formed by intersection of at least two radiation patterns emanating from the irradiation ports.

The wavelength of the radiation is in the range of about 1.4 $\mu$m to 3.2 $\mu$m.

The system further comprises a membrane located between the corneal surface and the irradiation ports, the membrane adapted to transmit light to the cornea from the irradiation port.

The system further comprises inspection means adapted to observe and evaluate the shrinkage of the collagenous tissue while the radiation is introduced to the stroma.

The system further comprises inspection means adapted to observe and evaluate the shrinkage of the collagenous tissue after said radiation is introduced to the stroma.

The inspection means comprise a biomicroscope ad a slit lamp.

BRIEF DESCRIPTION OF THE DRAWINGS

FIG. 1A is an exploded perspective view of an LTK system in accordance with a second preferred embodiment of the present invention.

FIG. 6 is an exploded perspective view of an LTK system in accordance with an alternative embodiment of the present invention.

DESCRIPTION OF THE PREFERRED EMBODIMENTS

Figure 1:
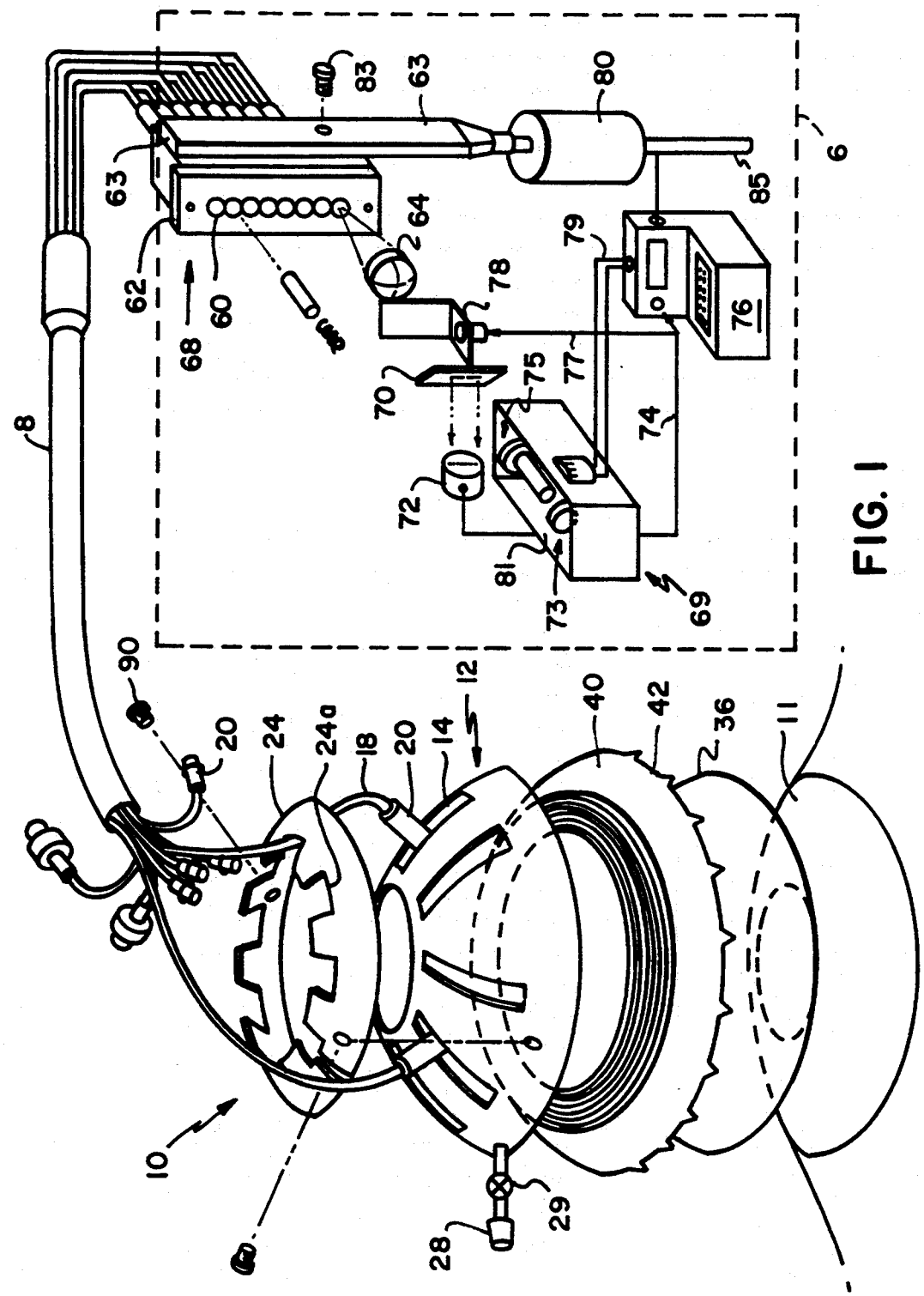
FIG. 1 is an exploded perspective view of a laser thermokeratoplasty (LTK) system in accordance with a preferred embodiment of the present invention.

Referring to FIG. 1, a fiber optic multi-fiber delivery system for performing laser thermokeratoplasty includes a laser light generation and coupling system 6, a fiber optic bundle 8, and a fiber optic cap assembly 10. Fiber optic cap assembly 10 includes a thornton ring 40, a rigid dome 12, with eight individual fibers 18 placed in tracks 14 and held in position by a spacer ring 24. Spacer ring 24 sets the proper placement of the individual fiber end housings 20 of optical fibers 18. A prophylactic membrane 36 is placed on cornea 11 and held in place by small protrusions 42 of thornton ring 40 (e.g., protrusions which may project 50 microns and have a corresponding width). The protrusions penetrate prophylactic membrane 36 and the corneal surface to hold thornton ring 40 in place during the laser thermokeratoplasty.

Rigid dome 12, fabricated of stainless steel, engineering plastic, or other suitable dimensionally stable material, is held on thornton ring 40 by creating a vacuum inbetween the two members or using a snap-on connector. Spacer ring 24 formed by two half rings is attached to rigid dome 12 using locator screws 90 and is used to set the placement of the fibers. The edges 24A of spacer ring 24 are shaped to allow placement of the individual fibers in a desired position. The invention envisions selecting a spacer ring from a set of several spacer rings 24 of different shapes that correspond to different geometric patterns for producing desired shapes of the cornea. Laser light generation and coupling system 6 enables coupling of the laser light into each individual fiber arranged into a linear array (shown in FIGS. 1 and 4), or a circular array (shown in FIG. 4B); however, other arrangements are also possible.

Figure 2:
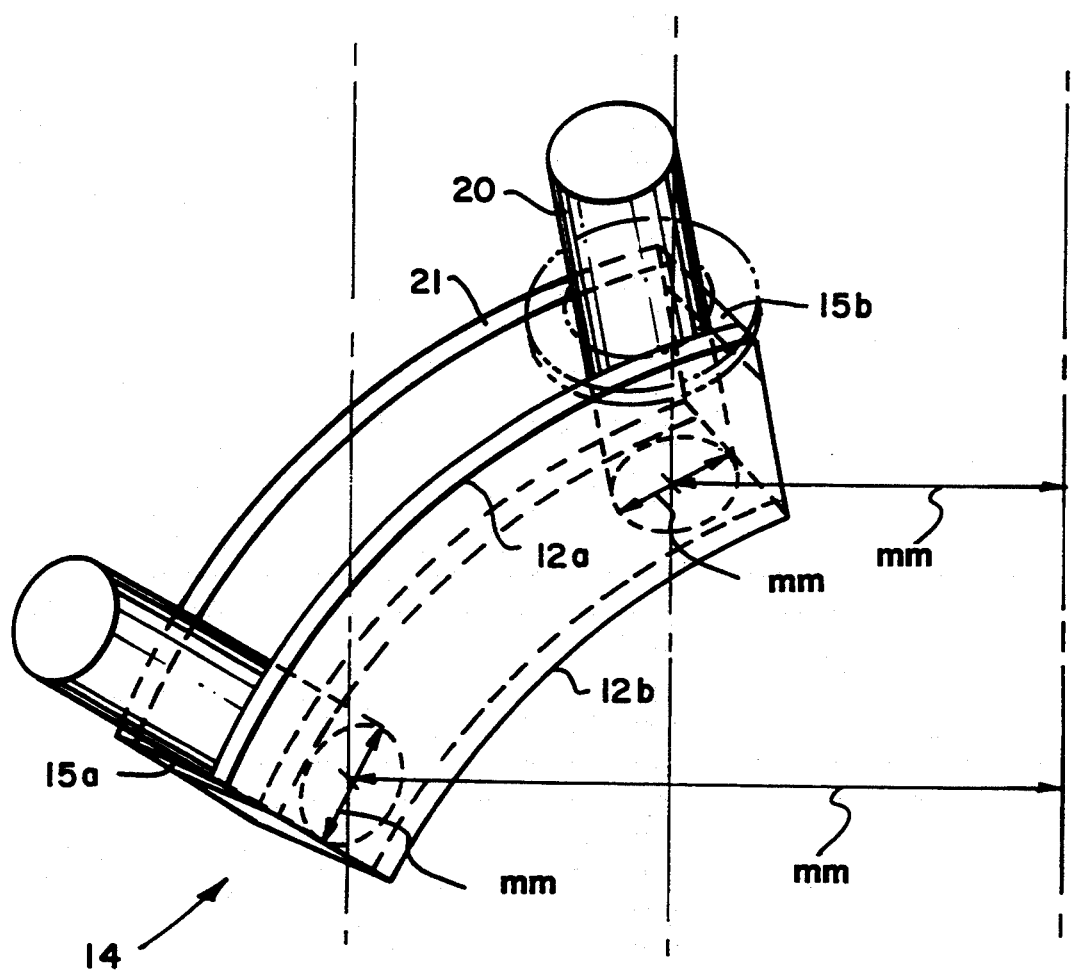
FIG. 2 is a schematic, perspective view of one track of a fiber optic cap assembly of the system of FIGS. 1 or 1A with a fiber end housing shown in two extreme positions.

FIG. 2 schematically shows one of the eight fiber end housings 20 that are mounted for adjustable movement in respective tracks 14. Tracks 14 are symmetrically arranged about the dome and dispersed in a pattern that converges on the optical axis of the eye. The fiber end housing 20 moves from an outer stop 15A, located at a vertically projected circle of about 4.5 mm radius, to an inner stop 15B, located at a projected circle of about 2.5 mm radius. Also referring to FIG. 2A, housing 20 is tightly positioned onto the surface of the IR (infra-red) transmitting membrane 36 that serves prophylactic purposes. Rigid dome 12 comprises an inner wall 12A and an outer wall 12B, both of which confine a fiber cup 25 radially. A washer spring 26 presses against a fiber support ring 21 and forces fiber cup 25 in contact with IR transmitting membrane 36 in the direction normal to the spherical surface (i.e., radial direction). In addition to the radial confinement, a tension spring 22 pulls fiber end housing 20 toward the lowest position defined by outer stop 15A. This action is balanced by spacer ring 24 that holds housing 20 in place in accordance with the location of the edge 24A of the preselected ring. The lateral movement of housing 20 is restrained by tracks 14.

Initially, membrane 36 and thornton ring 40 are placed on the corneal surface. Position of the thornton ring relative to the cornea does not change during the procedure. Dome 12 is affixed to thornton ring 40 using vacuum. A vacuum chamber 30 located between thornton ring 40 and rigid dome 12 is sealed by two 0-rings 31A and 31B. To create vacuum, a vacuum nozzle 28 with a vacuum valve 29 is attached to a vacuum pump (not shown in FIG. 2A). The pump is disconnected after a proper connection is created.

Figure 2A:
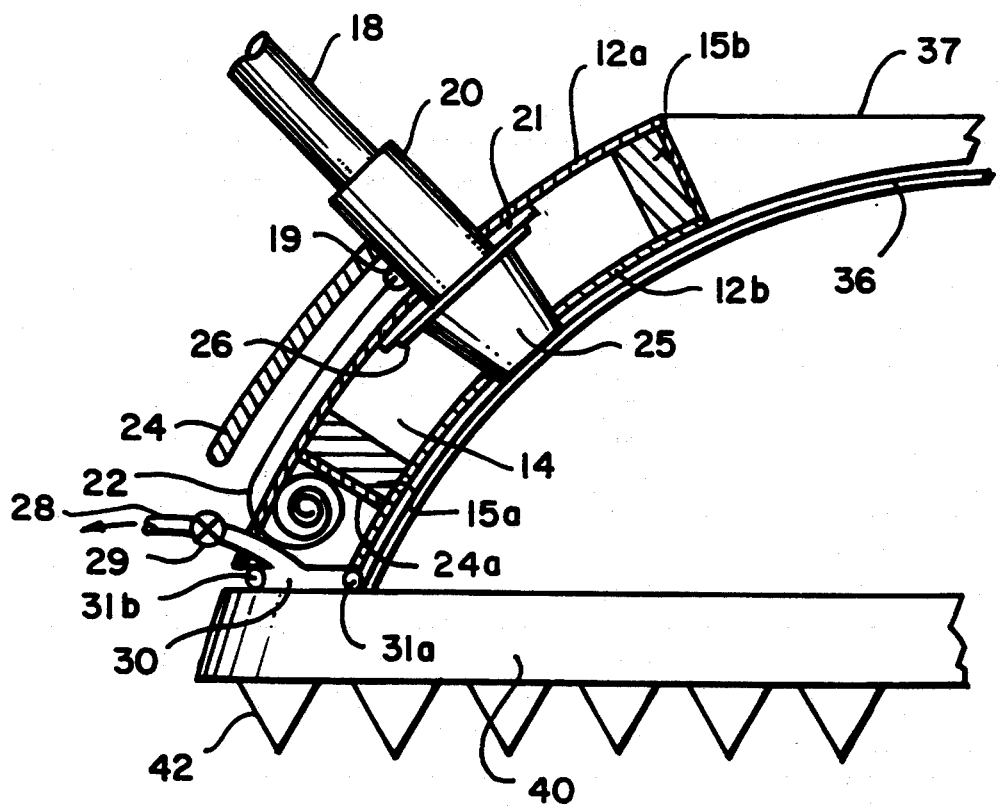
FIG. 2A is a detailed cross-sectional view of one track of the fiber optic cap assembly of FIG. 1.
Figure 2B:
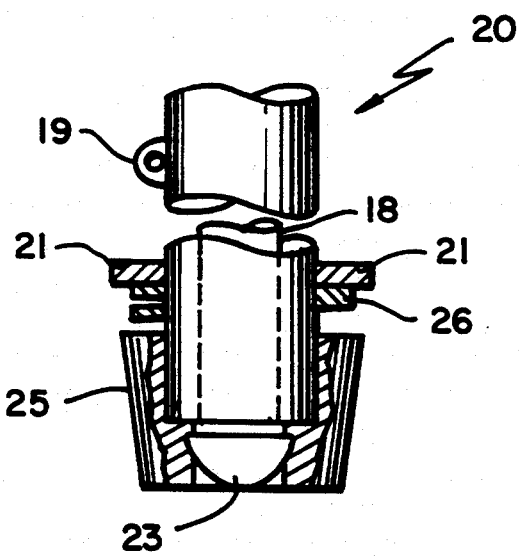
FIG. 2B is a cross-sectional view of the fiber end housing of FIG. 2A.
Figure 3:
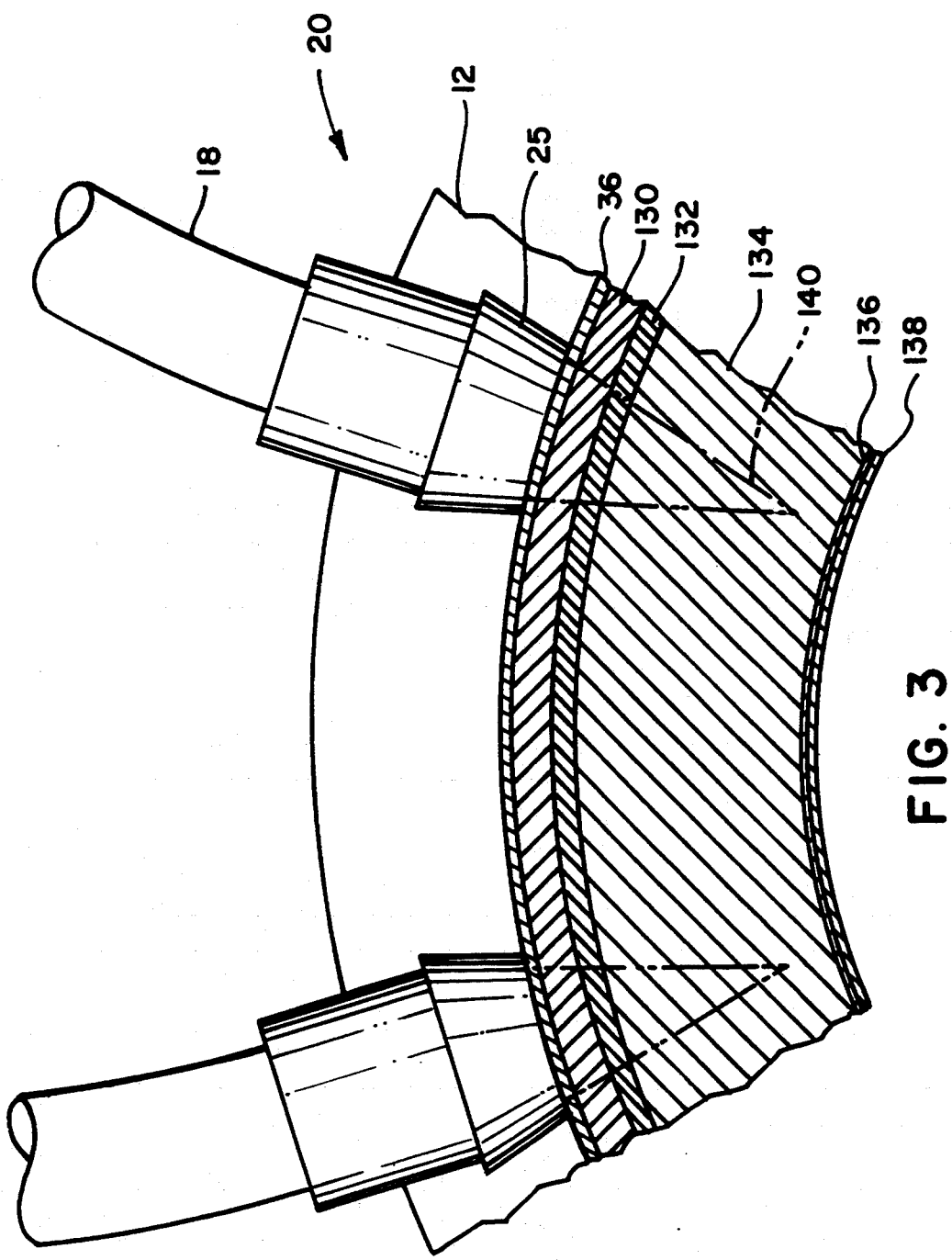
FIG. 3 is a cross-sectional view of the cornea with the system of FIG. 1 delivering radiation focused into cone-shaped treatment volumes in accordance with the present invention.

As shown in FIG. 2B, fiber housing 20 includes fiber cup 25, support ring 21, spring connector 19 and spring washer 26. Support ring 21 confines the whole fiber housing in track 14. Spring connector 19 is used to attach fiber 18 to a tension spring 22. Fiber cup 25 holds fiber 18 attached to a focusing lens 23 The fiber end is polished for optimal coupling of the light to lens 23. Lens 23 that forms an irradiation port focuses light into the stroma and creates a cone shaped isothermal region in the tissue. Alternatively, instead of using lens 23, the focusing can be achieved using a graded index (GRIN) fiber or by reducing the fiber's diameter at the end to form a convergent fiberoptic waveguide. Regardless of the particular details of construction employed, the term "irradiation port" as used herein refers to the output portion of the light-conducting structure of the delivery system by which the radiation is directed to the cornea. In order to properly couple the light into the stroma and eliminate reflections, it is important that the refractive index of prophylactic membrane 36 is selected to provide transition between the refractive indexes of lens 23 and the cornea. The refractive indexes can be also matched using a fluid medium located in fiber cup 25. The refractive index of the fluid provides transition between the refractive index of the fiber and the cornea. As the light passes from lens 23 through light transmitting membrane 36 to the stroma, it is absorbed in the stroma as shown in FIG. 3.

Referring to FIG. 1, at their light receiving end the individual optical fibers of fiber bundle 8 are assembled into a connector body 62. Connector body 62 is attached to a locator rod 63 which is connected to a shaft 85 of a linear motor 80. Linear motor 80 displaces connector body 62 so that each individual, polished fiber face 60 of fiber 18 in turn is placed in the laser light beam to couple the beam into the fiber. The face of each fiber 18 is polished to achieve optimal coupling of the laser light. The laser beam is generated in a resonator cavity 71 of a YAG laser 69 and exits the laser through an output coupler 75. The beam is directed to face 60 of fiber 18 through a beam splitter 70 and focused by a focusing lens 64. The amount of radiation delivered to each fiber is controlled by beam splitter 70, a light meter 72, and a shutter 78. Beam splitter 70 redirects a fraction of the emitted light to light meter 72 that sends a signal to laser 69 and a control system 76. The whole radiation delivery is controlled by control system 76 that governs the movement of linear motor 80 and the operation of laser 69 and shutter 78. Control system 76 contains different programs specifying the amounts of energy to be delivered to each individual fiber corresponding to different selected treatments.

Prophylactic membrane 36 (FIGS. 1, 1A and 2A) is made of quartz or an IR transmitting plastic. Each irradiation port of end housing 20 is tightly coupled to membrane 36. When the membrane is applied to the eye, a solution can be introduced between membrane 36 and the corneal surface to provide better coupling of light and to match the refractive indexes, as discussed above.

Figure 4:
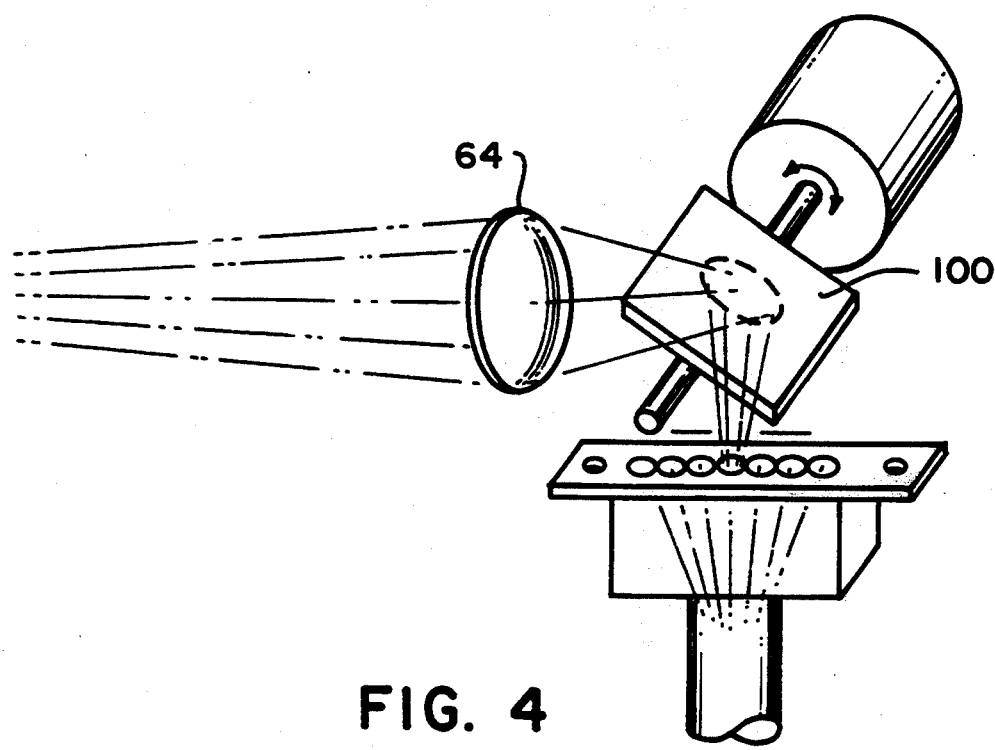
FIG. 4 is a detailed view of an optic system for directing light into individual fibers arranged in a linear pattern.
Figure 4A:
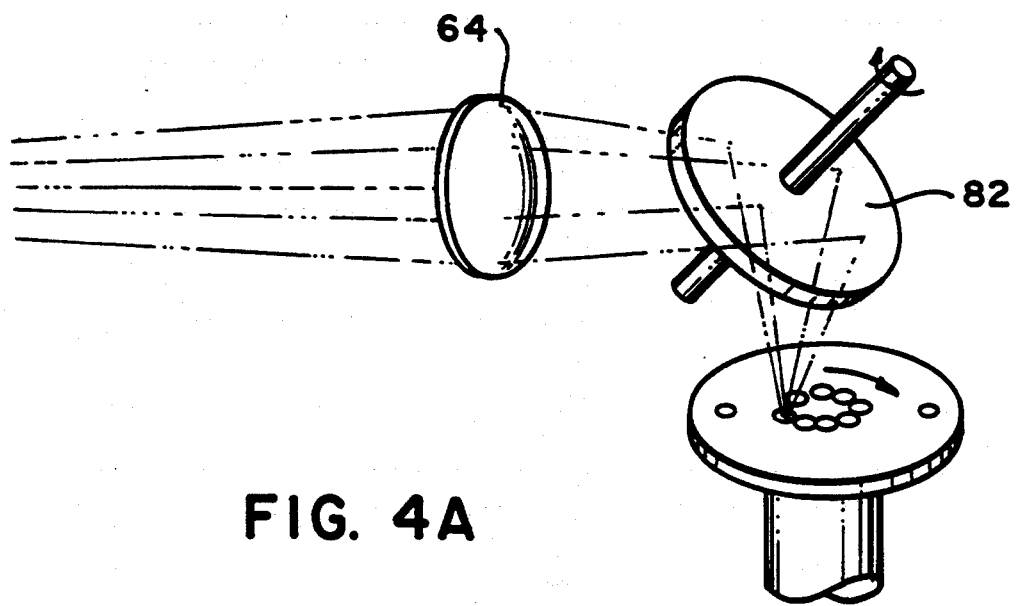
FIG. 4A is a detailed view of an optic system for directing laser light into individual fibers arranged in a circular pattern.

FIGS. 4 and 4A show two arrangements of sequential coupling of the laser beam into the individual fibers. In a linear arrangement of the fibers (FIG. 4), an oscillating mirror 100 is used to deliver light focused by imaging lens 64 to the individual fibers. If a circular array of optical fibers is used, a wobbolating mirror 110 is used to couple the light into the individual fibers. An irradiation system, such as the one shown in FIG. 1, delivers precise amounts of thermal energy sequentially to the individual coagulation sites within the stroma.

Figure 4B:
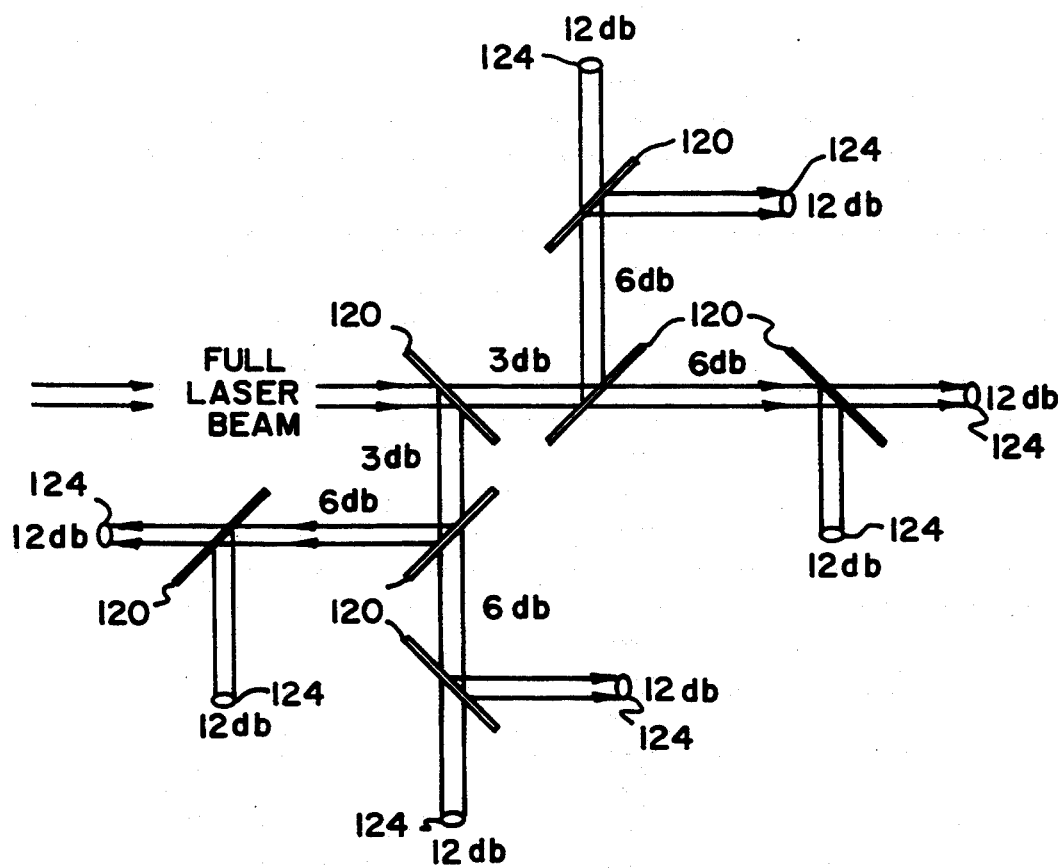
FIG. 4B is a schematic arrangement of beam splitters creating eight simultaneous equal intensity beams.

Alternatively, all fibers can be illuminated simultaneously using the system of beam splitters of FIG. 4B. The simultaneous illumination system utilizes a set of seven beam splitters 120 that equally divide the laser light and couple simultaneously the individual beams of light 124 into the fiber faces 60. Each beam splitter 120 reflects 50% of the incoming light and transmits the other 50%. The resulting eight beams are simultaneously focused and coupled to the fibers FIG. 3 is a cross-sectional view of the cornea with the LTK delivery system of FIG. 1 attached on the corneal surface. As shown in detail, the cornea consists of the epithelium 130, Bowman's membrane 132, the relatively thick stroma 134, Descemet's membrane 136, and the endothelium 138 located in the posterior of the cornea. Light transmitting membrane 36 located on the epithelium surface has the irradiation port of cup 25 tightly coupled to its anterior surface using dome 12. The laser light delivered by fiber 18 is focused into a shallow conical treatment volume 140 that penetrates the cornea to a depth of about 400 to 450 $\mu$m. The focused beam defines the coagulation pattern which is generally coincident with the cone shaped isothermal region 140. Thus, most of the infra-red energy is dissipated in the collagen fibers of the stroma which is the targeted tissue of the cornea, but some substantially smaller amounts of energy are dissipated in the epithelium and Bowman's membrane. Focusing of the energy to the above-described depth prevents damage to the highly sensitive Descemet membrane and the underlying endothelial layer since little energy is dissipated beyond the focal point of cone 140 located in the stroma.

Another preferred embodiment of a multi-fiber delivery system for performing the laser thermokeratoplasty is shown in FIG. 1A. In this embodiment, each fiber end housing 20A located in track 14 includes three fibers 18. The fiberoptic cap assembly 10A is used substantially in the same way as the previously described embodiment of FIG. 1. Spacer ring 24 with edges 24A holds fiber end housing 20A in place within tracks 14 in a similar way as shown in FIGS. 2, 2A and 2B. Each of the three fibers 18 of fiber end housing 20A has its irradiation port pressed against prophylactic membrane 36 located on the globe of the eye. The irradiation ports are positioned in a preselected spatial relationship that defines intersection of the introduced radiation patterns. This enables controllable introduction of the radiation patterns that form the treatment volume in the stroma.

Figure 3A:
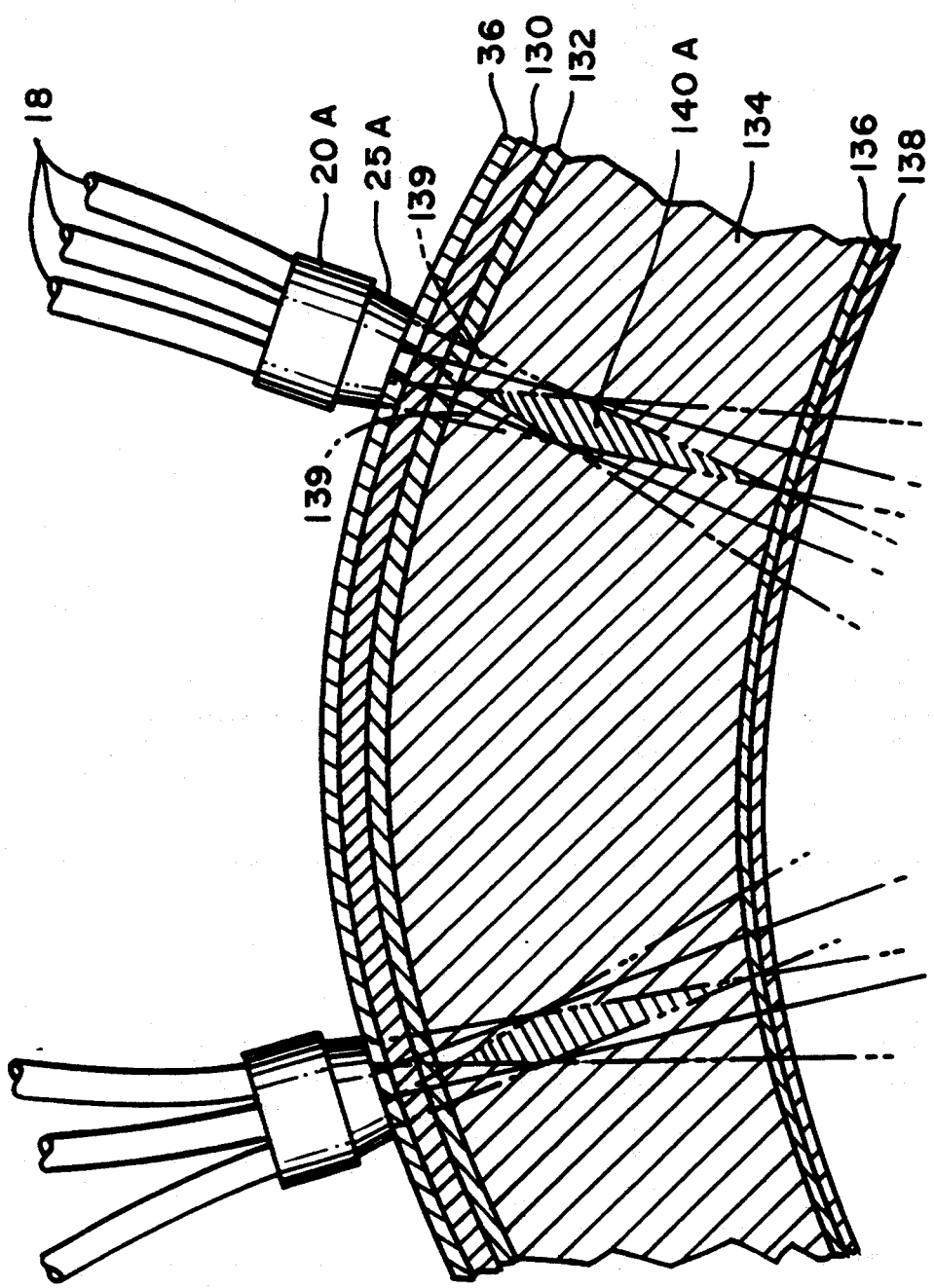
FIG. 3A is a cross-sectional view of the cornea with the system of FIG. 1A delivering radiation to the stroma and forming treatment volumes by intersection of multiple radiation patterns.

Referring to FIG. 3A, each radiation pattern 139 emanating from irradiation ports of fibers 18 carries energy substantially smaller than the energy necessary for thermal coagulation of the stromal tissue. Treatment volume 140A is formed by intersection of the three radiation patterns. In general, desired coagulation zones can be created by selecting appropriate number of fibers 18 positioned with their irradiation ports having desired spacing and angular relationship to each other. The depth, volume and energy profile of treatment volume 140A where the shrinkage occurs can be varied by attuning the spatial relationship of the introduced radiation patterns. For example, increasing the spacing and the angle between the irradiation ports will form a treatment volume of smaller size positioned closer to the corneal surface. In some embodiments wherein large separation of treatment volumes is required, each fiber 18 is placed in separate fiber end housing 20 and several fiber end housings located on the same track or on adjacent tracks are grouped together to form a set associated with one treatment volume. Furthermore, the introduction angle of the radiation pattern can be varied within the fiber end housing by adjusting the orientation of the irradiation port with respect to prophylactic membrane 36 and the corneal surface.

The treatment according to the present invention involves precise measurement of the shape of the cornea prior to treatment in order to determine the required geometric pattern of treatment volumes and corresponding coagulation zones. Then, a corresponding set of spacer rings 24 is selected to hold in place the fiber end housings 20 located in tracks 14 and to appropriately position the irradiation ports. The patient's cornea is anesthetized using a topical anesthetic and an eyelid speculum is used to retract the eyelid. The patient looks directly along a selected direction while prophylactic membrane 36 and thornton ring 40 are placed on the corneal surface. This aligns the patient's visual axis with the axis of assembly 10. The position can be verified using a surgical microscope and a fixation light. Only the prophylactic membrane and the thornton ring are in direct contact with the corneal surface. These two components are either disposable or will be sterilized after performing each procedure.

Small protrusions 42 hold the thornton ring in place. Next, all fiber end housings 20 are placed in the desired positions by attaching spacer ring 24 on rigid dome 36. Rigid dome 36 is affixed to thornton ring 40 by applying vacuum to vacuum port 29. Once the LTK delivery system 10 or 10A for the embodiment of FIG. 1A) is in place, the irradiation procedure using the laser light distribution and delivery system 6 is performed. The system uses a holmium: YAG solid state laser generating 2.1 $\mu$m wavelength radiation; however, other sources of infrared radiation can be used. It is expected that each treatment location will receive 400–600 mJ with about 15–25 mJ/pulse energy. Control system 76 automatically directs the appropriate number of pulses to each fiber. Approximately two seconds are usually needed to treat each spot. The coagulation can be observed using a biomicroscope and a slit lamp. For this purpose, the central open portion of rigid dome 12 is used.

In another embodiment, the inspection of the coagulating spot can be also performed using an additional inspection fiber that can be placed on tracks 14 near treatment fiber 18 that is used for the energy delivery. The inspection fiber is used for real time monitoring of the coagulation process by observing the scattered light. Alternatively, after the coagulation, the coagulated zone is illuminated using the treatment fiber and observed using the inspection fiber. A feedback signal obtained from the inspection fiber is used to automate the procedure.

After the laser thermokeratoplasty is performed, the corneal surface is rinsed using BSS solution and topical anesthetic is applied. Topical use of antibiotics and a patch for a few days is envisioned as a part of standard care.

Figure 5:
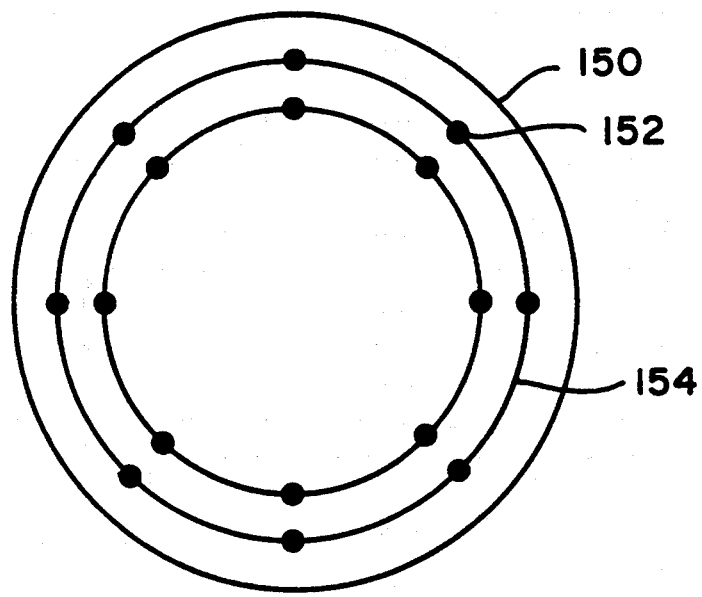
FIG. 5 is a plan view of a geometric exposure pattern for treatment of hyperopia.
Figure 5A:
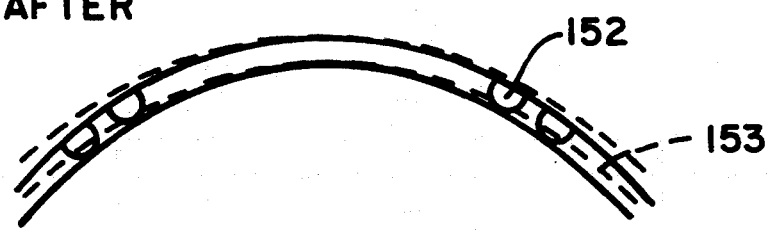
FIG. 5A is a cross-sectional view of the cornea treated by using the pattern of FIG. 5.

A plan view of exposure locations for treatment of the hyperopia are shown in FIG. 5. The corneal perimeter is shown as a circular ring 150. A typical treatment involves creation of 8 coagulation zones 152 located on ring 154. Depending on the degree of hyperopia, a different number of concentric circular rings 154 of irradiation is used. Two rings of irradiation, shown in FIG. 5, are usually used for the treatment of moderate hyperopia. The irradiation ports of the fibers 18 are repositioned from one treatment ring to the other by rotating a suitably configured spacer ring 24 or exchanging it for another. Change in the corneal curvature as a result of the laser-induced coagulation is shown in FIG. 5A. The peripheral contraction of the collagen fibers causes reduction of the corneal diameter and thus desired steepening of the corneal curvature occurs.

Figure 5B:
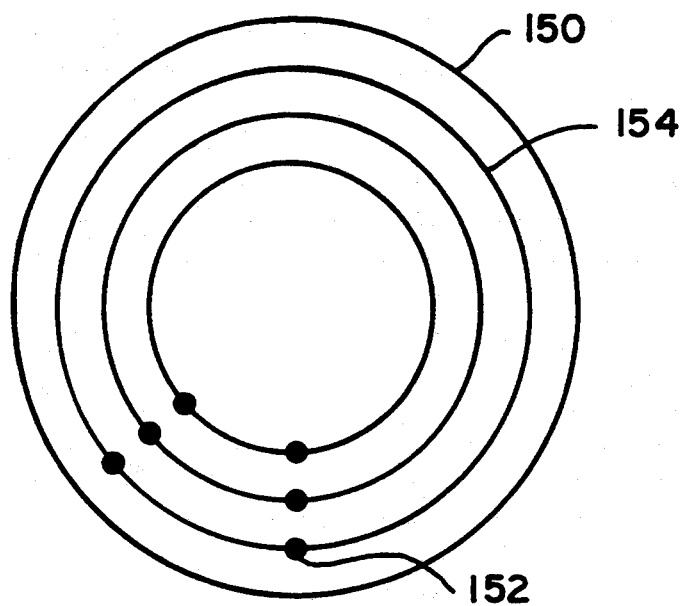
FIG. 5B is a plan view of a geometric exposure pattern for treatment of astigmatism.
Figure 5C:
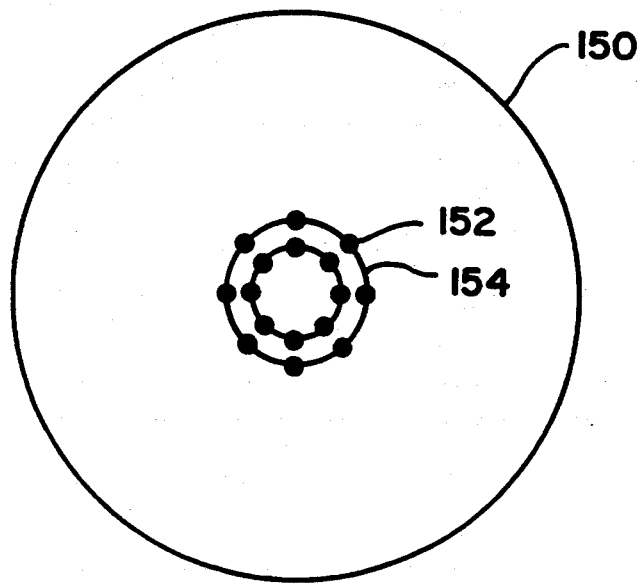
FIG. 5C is a plan view of a geometric exposure pattern for treatment of myopia.

Geometric patterns for the treatment of other refractive errors are shown in FIGS. 5B and 5C. To correct for astigmatism, a line of coagulation spots is used (FIG. 5B). Myopic correction is achieved by creating central coagulation regions (as shown in FIG. 5C) and thus flattening the corneal surface. It is expected that after the laser thermokeratoplasty treatment, the contracted fibers will relax somewhat; this is taken into account when designing the treatment pattern. The system enables precise and controlled creation of the coagulation spots, which is important for reproducibly altering the corneal shape.

Alternative Embodiments

Figure 6A:
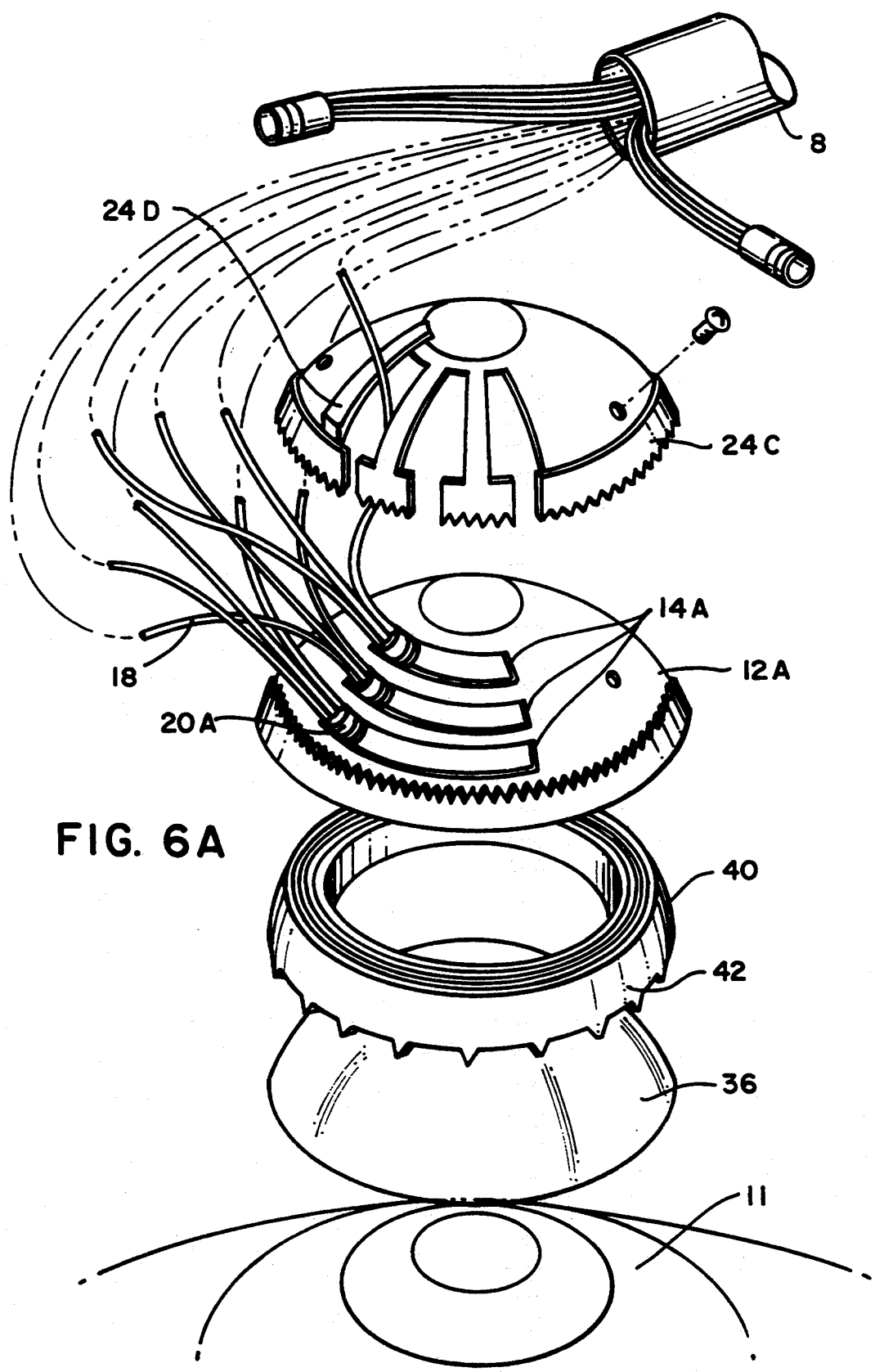
FIG. 6A is an exploded perspective view of an LTK system in accordance with another alternative embodiment of the present invention.

Referring to FIGS. 6 and 6A, in an alternative embodiment, the LTK system of FIGS. 1 and 1A includes a rigid dome 12A with three semi-circular tracks 14A holding fiber end housings 20 and 20A, respectively.

Prophylactic membrane 36 and thornton ring 40 are placed on the corneal surface 11. Rigid dome 12A is attached to thornton ring 40 using vacuum or some other easy to use connection. Fiber end housing 20 (or 20A) is positioned at the desired location on a preselected geometric pattern using a holding member 24C. Holding member 24C can be rotated to a different position with respect to dome 12A. The laser thermokeratoplasty is performed in the same way as for the embodiments of FIGS. 1 and 1A.

In an alternative embodiment of FIGS. 1 and 1A, the multi-fiber delivery system may include only two or three fibers located on tracks 14. This reduces complexity of the system. The irradiation port of housing 20 is placed at a desired radial location in track 14 using spacer ring 24. The system is constructed to displace the fibers on circular pattern 154 (FIG. 5) by rotating rigid dome 12 with respect to thornton ring 40. For precise rotation, both rigid dome 12 and thornton ring 40 have alignment marks that enable precise angular displacement of the irradiation ports. Thornton ring 40 remains fixedly attached to the cornea. The combined linear displacement of the fiber end housings within tracks 14 and rotational movement of rigid dome 12 with respect to thornton ring 40 allows the irradiation ports to move along any curve, e.g., circular or elliptical.

Other embodiments are within scope of the following claims.

We claim:

1. A thermokeratoplasty system for modifying corneal curvature of a cornea by localized thermal shrinkage of collagenous stromal tissue, said system comprising:
    means for inducing localized thermal shrinkage of the collagenous stromal tissue using electromagnetic radiation of a wavelength suitable for absorption in the stroma, said mean including a radiation-distributing device that introduces the electromagnetic radiation to a multiplicity of locations on the surface of the cornea according to a predetermined pattern selected to correspond to a desired modification of said cornea, and
    a positioning structure that positions said radiation-distributing device in close, fixed relationship to the cornea and introduces said radiation via said locations to treatment volumes in the stroma below the surface of the cornea to induce localized shrinkage of the collagenous stromal tissue to cause change in the corneal curvature.

2. The system of claim 1 wherein said radiation-distributing device delivers energy to each of said locations at an energy level substantially below the energy necessary for shrinkage of said collagenous stromal tissue and causes energy entering said locations to intersect to form said treatment volumes in the stroma in which the energy level is sufficient to induce shrinkage of the collagenous stromal tissue.

3. The system of claim 1 wherein said means includes a radiation source and said radiation-distributing device further comprises a radiation transmission system for receiving radiation from said source, the radiation reaching the cornea being emitted from a set of irradiation ports positioned corresponding to said locations.

4. A system for modifying curvature of a cornea by irradiating the cornea with electromagnetic radiation of a wavelength suitable for absorption in stromal tissue, said system comprising:
    a radiation source, optically coupled to a transmission system, that emits electromagnetic radiation of a wavelength suitable to induce localized thermal shrinkage of the collagenous stromal tissue of the cornea,
    said transmission system transmits controlled amounts of said radiation from said source,
    said transmission system having multiple irradiation ports for introduction of the electromagnetic radiation to the stroma,
    a positioning structure that positions said irradiation ports respectively at preselected relationships to the cornea, said relationships being selected to correspond to a desired modification of the cornea, and
    said irradiation ports, positioned at said preselected relationships direct the radiation to respective treatment volumes in the stroma in a cooperative manner to induce localized shrinkage of the collagenous stromal tissue to cause change in the corneal curvature.

5. The system of claim 4 or 3 wherein said positioning structure positions said irradiation ports according to a selectable geometric pattern relative to said cornea to create a specific distribution of treatment volumes in each of which said desired shrinkage can occur.

6. The system of claim 5 wherein each of said treatment volumes is formed by a radiation pattern emanating from one irradiation port.

7. The system of claim 5 wherein at least two of said ports are cooperatively arranged to cause said desired shrinkage to occur in a treatment volume formed by intersection of radiation patterns emanating from aid irradiation ports, energy of a single radiation pattern being substantially below the energy level necessary for shrinkage of said collagenous stromal tissue, said intersection of radiation patterns forming a treatment volume having sufficient energy to induce shrinkage of said collagenous stromal tissue.

8. The system of claim 7 wherein an adjustable device is provided to vary the spatial relationship of said ports to vary the conditions of intersection of the emitted radiation forming said treatment volumes.

9. The system of claim 5, wherein said positioning structure enables movement of said irradiation ports to selected different locations to change said preselected geometric pattern.

10. The system of claim 5 wherein said positioning structure is attachable to the surface of the cornea in a desired relationship to accurately position said irradiation ports with respect to said cornea.

11. The system of claim 10 further comprising prophylactic means placed between said surface of the cornea and said positioning structure.

12. The system of claim 11 wherein said prophylactic means comprise optical interface matching means for coupling said radiation form said irradiation ports to the cornea without substantial loss.

13. The system of claim 10 wherein said positioning structure includes an eye fixation means for holding said positioning structure at a selected location on said surface of the cornea while preventing movement of the eye.

14. The system of claim 13 wherein said eye fixation means comprises a thornton ring attached to said surface of the cornea by relatively small protrusions.

15. The system of claim 5 wherein said irradiation port includes focusing means for focusing said radiation within the stromal tissue.

16. The system of claim 15 wherein said focusing means and locations of said ports define each said treatment volume and the energy profile of delivered radiation to said treatment volume.

17. The system of claim 15 wherein said focusing means focus said radiation to a desired depth within the stromal tissue.

18. The system of claim 15 wherein said focusing means comprise a focusing lens.

19. The system of claim 15 wherein said focussing means comprise a convergent fiberoptic wave guide.

20. The system of claim 15 wherein said focusing means comprises a self-focusing fiber optic wave guide.

21. The system of claim 4 wherein said transmission system comprises a set of fiber optic wave guides each corresponding to a respective irradiation port, said irradiation ports being positioned according to a selectable geometric pattern relative to said cornea to create a specific distribution of treatment volumes, each said wave guide transmitting the radiation from said source to its respective irradiation port.

22. The system of claim 21 wherein each said irradiation port is positioned at a selected location according to said preselected geometric pattern relative to the cornea and adapted to introduce a radiation pattern that forms said treatment volume.

23. The system of claim 21 wherein said irradiation ports are positioned at locations according to said preselected geometric pattern relative to the cornea, said irradiation ports introducing radiation patterns that form said treatment volume at their intersection, energy of a single radiation pattern being substantially below the energy level necessary for shrinkage of the collagenous stromal tissue, said treatment volume created by said intersection of at least two of said radiation patterns having energy sufficient to induce shrinkage of the collagenous stromal tissue.

24. The system of claim 22 further comprising a distribution system, said distribution system distributing desired amounts of energy from said radiation source in a predetermined sequence to each of said fiber optic waveguides.

25. The system of claim 23 further comprising a distribution system, said distribution system distributing simultaneously desired amounts of said radiation from said radiation source to all of said fiber optic waveguides.

26. The system of claim 22 further comprising a distribution system, said distribution system distributing desired amounts of said radiation from said source simultaneously to all of said fiber optic waveguides.

27. The system of claim 5 wherein said irradiation ports comprise optical interface matching means for coupling the radiation to the cornea without substantial radiation loss.

28. The system of claim 27 wherein said optical interface matching means includes a fluid medium.

29. The system of claim 4 or 3 wherein said positioning structure comprises:
 a rigid hemi-spherically shaped member positionable upon the surface of said cornea in a desired relationship to the shape of the cornea,
 at least two tracks located in said rigid member at spaced apart positions, each track retaining at least one said irradiation port within said rigid member and enabling movement of said irradiation port to selected different locations within said tracks, and
 a holding member that holds said irradiation ports at said selected different locations within said tracks, said holding member enabling said ports to reside in locations according to said preselected geometric pattern.

30. The system of claim 29 wherein said positioning structure further comprises a ring shaped member having small protrusions constructed to be affixed to said surface of the cornea, said ring shaped member being connectable to said rigid hemi-spherically shaped member and being adapted to maintain said irradiation ports at said selected different locations within said tracks.

31. The system of claim 30 wherein said positioning structure further comprises a membrane located between said surface of the cornea and said ring shaped member, said membrane transmitting radiation to said cornea from said irradiation ports.

32. A thermokeratoplasty system for modifying curvature of a cornea by irradiating the cornea to deliver thermal energy to collagenous stromal tissue, said system comprising:
 a radiation source that emits electromagnetic radiation of a wavelength suitable to induce localized thermal shrinkage of the collagenous stromal tissue of the cornea,
 a radiation-distributing device that introduces Controlled amounts of said electromagnetic radiation from said source to a multiplicity of irradiation ports located on locations on the surface of the cornea,
 a rigid hemi-spherically shaped member positionable upon the surface of the cornea in a desired relationship to the cornea,
 at least two tracks located in said rigid member at spaced apart positions, each track retaining at least one said irradiation port within said rigid member and enabling movement of said irradiation port to a selected location on a preselected geometric pattern, said preselected geometric pattern being selected to correspond to a desired modified shape of said cornea, a holding member that holds said irradiation ports at said selected locations within said tracks according to said preselected geometric pattern, a ring shaped member having small protrusions affixable to the surface of the cornea, said ring shaped member being connectable to said rigid spherically shaped member to maintain said irradiation ports at said locations, and said irradiation ports, positioned at said selected locations, that introduce said radiation to be absorbed in selected treatment volumes of the stroma to induce shrinkage of the collagenous stromal tissue and cause change in the corneal curvature to said desired modified shape.

33. The system of claim 32 wherein said ring shaped member is connectable to said rigid hemi-spherically shaped member using a vacuum created between said ring shaped member and said rigid hemi-spherically shaped member.

34. The system of claim 33 wherein said ring shaped member is connectable to said rigid hemi-spherically shaped member in a manner that enables relative rotational movement of the two members.

35. The system of claim 4, 1 or 32 further comprising computer control system that governs distribution of said radiation from said source to each irradiation port in accordance with locations of irradiation ports and said desired modification of the cornea.

36. The system of claim 32 wherein said treatment volumes introduced into said stroma via said ports comprise a conical shape.

37. The system of claim 32 wherein said treatment volumes of the stroma are formed by intersection of at least two radiation patterns emanating from said irradiation ports.

38. The system of claim 4 or 32 wherein said wavelength is in the range of about 1.4 μm to 3.2 μm.

39. The system of claim 32 further comprising a membrane located between the corneal surface of the cornea and said irradiation ports, said membrane transmits light to the cornea from said irradiation port.

40. The system of claim 4, 1 or 32 further comprises an inspection system that observes and evaluates said shrinkage of the collagenous stromal tissue while said radiation is introduced to the stroma.

41. The system of claim 4, 1 or 32 further comprises an inspection system that observes and evaluates said shrinkage of the collagenous stromal tissue after said radiation is introduced to the stroma.

42. The system of claim 40 wherein said inspection means comprise a biomicroscope and a slit lamp.

43. A method of modifying the corneal curvature by irradiating the cornea to deliver thermal energy to the stroma comprising:

(a) providing a radiation source for emitting electromagnetic radiation of a wavelength suitable to induce localized shrinkage of the collagenous stromal tissue of the cornea, (b) providing a radiation-distributing device for receiving and distribute said radiation to a set of irradiation ports corresponding to locations for delivering radiation to the stroma, (c) positioning said irradiation ports respectively according to a preselected geometric pattern relative to said cornea, said pattern being selected to correspond to a desired modification of the cornea, (d) generating electromagnetic radiation of a wavelength suitable for absorption in the stroma.

(e) transmitting controlled amounts of said radiation from said source to at least one of said irradiation ports, and (f) introducing to the cornea, at said irradiation ports, said radiation for absorption in treatment volumes of the stroma in a cooperative manner to induce desired thermal shrinkage of the collagenous stromal tissue and to cause change in the corneal curvature.

44. The method of claim 43 wherein said irradiation ports are positioned according to a preselected geometric pattern relative to the shape of the cornea to create a specific distribution of treatment volumes.

45. The method of claim 44 wherein said step of introducing said radiation is performed to form said treatment volume by a radiation pattern emanating from one irradiation port.

46. The method of claim 44 wherein said step of introducing said radiation is performed to form said treatment volume by intersection of radiation patterns emanating from at least two irradiation ports, whereby the energy of a single radiation pattern being substantially below the energy level necessary for shrinkage of the collagenous stromal tissue, said intersecting radiation patterns forming a treatment volume having sufficient energy to induce shrinkage of the collagenous stromal tissue.

47. The method of claim 46 wherein said locations of said irradiation ports are varied in a controllable manner to vary the conditions of intersection of said radiation patterns.

48. The method of claim 44, 45 or 46 further comprising:

(a) moving said irradiation ports to different locations according to a preselected geometric pattern, (b) transmitting controlled amounts of said radiation from said source to each of said irradiation ports, and (c) introducing to the cornea, at said irradiation ports, treatment volumes of said radiation for absorption in the stroma to induce shrinkage of the collagenous stromal tissue and to cause change in the corneal curvature to a desired modified shape.

49. The method of claim 48 wherein said step of moving said irradiation ports is performed continually along a path while simultaneously introducing said radiation to the stromal tissue in order to form said treatment volumes, said path being chosen in correlation with said preselected geometric pattern.

50. The method of claim 44 or 45 wherein said step of transmitting said controlled amounts of radiation is performed sequentially to said multiple irradiation ports.

51. The method of claim 46 wherein said step of transmitting said controlled amounts of radiation is performed simultaneously to a set of said irradiation ports constructed to introduced intersection radiation patterns forming said treatment volumes.

52. The method of claim 44, 45 or 46 wherein said step of transmitting said controlled amounts of radiation is performed simultaneously to all said multiple irradiation ports.

53. The method of claim 44, 45 or 46 wherein said step of introducing to the cornea said radiation comprises focussing said radiation to form said treatment volume, said treatment volume extending to a depth of less than about 450 μm in the cornea.

54. The method of claim 44, 45 or 46 further comprising a step of inspecting said treatment volumes in the stroma.

55. The method of claim 54 wherein said step of inspecting said treatment volumes in the stroma is performed after causing said shrinkage of the collagenous stromal tissue.

56. The method of claim 54 wherein said step of inspecting said treatment volumes of the stroma is performed while introducing said radiation for absorption in the stroma.

* * * * *